(12) United States Patent
Agrawal

(10) Patent No.: US 7,173,014 B2
(45) Date of Patent: Feb. 6, 2007

(54) HIV-SPECIFIC SYNTHETIC OLIGONUCLEOTIDES AND METHODS OF THEIR USE

(75) Inventor: Sudhir Agrawal, Shrewsbury, MA (US)

(73) Assignee: Idera Pharmaceuticals Inc., Cambridge, MA (US)

( * ) Notice: Subject to any disclaimer, the term of this patent is extended or adjusted under 35 U.S.C. 154(b) by 447 days.

(21) Appl. No.: 09/896,692

(22) Filed: Jun. 29, 2001

(65) Prior Publication Data

US 2003/0100521 A1 May 29, 2003

Related U.S. Application Data

(63) Continuation of application No. 08/914,827, filed on Aug. 19, 1997, now abandoned.

(51) Int. Cl.
- A01N 43/04 (2006.01)
- C12P 19/34 (2006.01)
- C12N 15/63 (2006.01)
- C07H 21/02 (2006.01)
- C07H 21/04 (2006.01)

(52) U.S. Cl. ............... 514/44; 435/6; 435/91.1; 435/455; 536/23.1; 536/24.32; 536/24.5

(58) Field of Classification Search ............ 435/6, 435/91.1, 91.31, 455, 458; 536/23.1, 24.32, 536/24.5; 514/1, 2, 44
See application file for complete search history.

(56) References Cited

U.S. PATENT DOCUMENTS

| | | | |
|---|---|---|---|
| 4,309,404 A | 1/1982 | DeNeale et al. | 424/32 |
| 4,309,406 A | 1/1982 | Guley et al. | 424/32 |
| 4,556,552 A | 12/1985 | Porter et al. | 424/32 |
| 4,704,295 A | 11/1987 | Porter et al. | 424/32 |
| 4,806,463 A | 2/1989 | Goodchild et al. | 435/5 |
| 5,470,702 A | 11/1995 | Hovanessian et al. | 435/5 |
| 5,591,721 A | 1/1997 | Agrawal et al. | 514/44 |
| 5,627,277 A * | 5/1997 | Cohen et al. | 536/25.4 |
| 5,652,355 A | 7/1997 | Metelev et al. | 536/24.5 |
| 5,652,356 A | 7/1997 | Agrawal | 536/24.5 |
| 5,801,154 A * | 9/1998 | Baracchini et al. | 514/44 |
| 6,608,035 B1 | 8/2003 | Agrawal et al. | 514/44 |
| 6,645,943 B1 | 11/2003 | Agrawal et al. | 514/44 |
| 2002/0168340 A1 | 11/2002 | Agrawal | |

FOREIGN PATENT DOCUMENTS

| | | |
|---|---|---|
| WO | WO 94/08004 | 4/1994 |
| WO | WO 95/11813 | 7/1995 |
| WO | WO96/12497 | 5/1996 |
| WO | WO 97/06662 A | 2/1997 |
| WO | WO 98/40058 | 9/1998 |

OTHER PUBLICATIONS

Agrawal, S. et al. Molecular Med. Today, vol. 6, pp. 72-81 (2000).*
S. Crooke. Antisense Res and Application, Chapter 1, pp. 1-50 (S. Crooke, ed. Springer-Verlag, Publi.) (1998).*
Chirila, T. et a. Biomaterials, vol. 23, pp. 321-342 (2002).*
Branch, A. Trends in Biochem. Sci. vol. 23, pp. 45-50 (1998).*
Pihl-Carey, K. BioWorld Today, vol. 10, pp. 1-2 (1999).*
Peracchi, A. et al. Rev. Med. Virol., vol. 14, pp. 47-64 (2004).*
Milner et al. (1977) "Selecting Effective Antisense Reagents On Combinatorial Oligonucleotide Arrays," Nature Biotech. 15:537-541.
Wickstrom (1986) "Oligodeoxynucletide Stability in Subcellular Extracts and Culture Media," J. Biochem. Biophys. Meth. 13:97-102.
Zamecnik et al. (1986) "Inhibition of Replication and Expression of Human T-cell Lymphotropic Virus Type III in Cultured Cells by Exogenous Synthetic Oligonucleotides Complementary to Viral RNA," Proc. Natl. Acad. Sci. USA 83:4143-4147.
Agrawal et al. (1987) "Oligodeoxynucleoside Methylphosphonates: Synthesis and Enzymic Degradation," Tetrahedron. Lett. 28 (31):3539-3542.
Agrawal et al. (1988) Oligodeoxynucleoside Phosphoroamidates and Phosporothioates As Inhibitors of Human Immunodeficiency Virus, Proc. Natl. Acad. Sci. USA 85:7079-7083.
Goodchild et al. (1988) "Inhibition of Human Immunodeficiency Virus Replication by Antisense Oligodeoxynucleotides," Proc. Natl. Acad. Sci. USA 85:5507-5511.
Matsukura et al. (1988) "Synthesis of Phosphorothioate Analogues of Oligodeoxyribonucleotides and Their Antiviruval Activity Against Human Immunodeficiency Virus (HIV)," Gene 72:343-347.
Sarin et al. (1988) "Inhibition of Acquired Immunodeficiency Syndrome Virus by Oligodeoxynucleoside Methylphosphonates," Proc. Acad. Sci. USA 85:7448-7451.
Agrawal et al. (1989) "Inhibition of Human Immunodeficiency Virus in Early Infected and Chronically Infected Cells by Antisense Oligodeoxynucleotides and Their Phosphorothioate Analogues," Proc. Natl. Acad. Sci. USA 86:7790-7794.
Matsukura et al. (1989) "Regulation of Viral Expression of Human Immunodeficiency Virus In Vitro by an Antisense Phosphorotioate Oligodeoxynucleotide Against rev(art/trs) In Chronically Infected Cells," Proc. Natl. Acad. Sci. USA 86:4244-4248.
Gennaro (ed.) (1990) Remington's Pharmaceutical Sciences (18th Ed.) Mack Publishing Co., Easton, PA.
Uhlmann et al. (1990) "Antisense Oligonucleotides: A New Therapeutic Principle," Chem. Rev. 90:543-583.
Agrawal (1991) in Prospects for Antisense Nucleic Acid Therapy of Cancer and AIDS, (Wickstron, ed.) Wiley-Liss, Inc., pp. 143-158.
Harrison et al. (1991) in RNA Tumor Viruses (Coffin et al., eds.) Cold Spring Harbor Laboratory, Cold Spring Harson, NY, p. 235).

(Continued)

Primary Examiner—Jane Zara
(74) Attorney, Agent, or Firm—Wilmer Cutler Pickering Hale and Dorr LLP

(57) ABSTRACT

Disclosed are synthetic oligonucleotides having a nucleotide sequences specifically complementary to nucleotides 324 to 345 of a conserved gag region of the HIV-1 genome, the oligonucleotide consisting of 21 nucleotides which are linked via phosphorothioate internucleotide linkages. Also disclosed are methods for inhibiting and treating HIV-1 and HIV-2 infection.

3 Claims, 3 Drawing Sheets

OTHER PUBLICATIONS

Vickers et al. (1991) "Inhibition of HIV-LTR Gene Expression by Oligonucleotides Targeted to the TAR Element," *Nucleic Acids Res.* 19:3359-3368.

Agrawal (1992) "Antisense Oligonucleotides as Antiviral Agents," *Trends in Biotechnology* 10:152-158.

Agrawal et al. (1992) "Cellular Uptake and Anti-HIV Activity in Oligonucleotides and Their Analogs," *Gene Regulation: Biology of Antisense RNA and DNA* (Erickson and Izant, eds.) Raven Press Ltr., New York, pp. 273-283.

Matsukura et al. (1992) "A New Concept in AIDS Treatment: An Antisense Approach and Its Current Status Towards Clinical Application," *Prospects for Antisense Nucleic Acid Therapy of Cancer and AIDS*, Wiley-Liss, Inc., pp. 159-178.

Tang et al. (1993) "Self-Stabilized Antisense Oligodeoxynucleotide Phosphorothioates: Properties and Anti-HIV Activity," *Nucleic Acids Res.* 20:2729-2735.

Brown (1994) "A Brief History of Oligonucleotide Synthesis. Protocols for Oligonucleotides and Analogs," *Methods in Molecular Biology* 20: 1-8.

Froehler (1994) "Oligodeoxynucleotide Synthesis," *Methods in Molecular Biology* 20:63-80.

Sonveaux (1994) "Protecting Groups in Oligonucleotide Synthesis," *Methods in Molecular Biology* 26:1-72.

Agrawal et al. (1995) "Tissue Distribution and *In Vivo* Stability in Rats of a Hybrid Antisense Oligonucleotide Following Oral Administration," *Biochem. Pharmacol.* 50(4):571-576.

Iyer et al. (1995) "A Novel Nucleoside Phosphoroamidite Synthon Derived From 1R, 2S-Ephedrine," *Tetrahedron Asymmetry* 6:1051-1054.

Krieg et al. (1995) "CpG Motifs in Bacterial DNA Trigger Direct B-Cell Activation," *Nature* 374:546-549.

Gewirtz et al. (1996) "Facilitating Oligonucleotide Delivery: Helping Antisense Deliver On Its Promise," *Proc. Natl. Acad. Sci. USA* 93:3161-3163.

Rojanasakul (1996) "Antisense Oligonucleotide Therapeutics," *Adv. Drug Del. Rev.* vol. 18:115-131.

Zhao et al. (1996) "Effect of Different Chemically Modified Oligodeoxynucleotides on Immune Stimulation," *Biochem. Pharmacol.* 51(2):173-182.

Zhang et al. (1996) "Pharmacokinetics and Tissue Disposition of a Chimeric Oligodeoxynucleosider Phosphorothioate in Rats After Intravenous Administration," *J. Pharmacol. Expt. Thera.* 278:1-5.

Agrawal, et al. (1992) "GEM*91—An Antisense Oligonucleotide Phosphorothioate as a Therapeutic Agent for AIDS", *Antisense Res. Dev.* 2:261-266.

Agrawal et al. (1994) "Potential for HIV-1 Treatment with Antisense Oligonucleotides", *J. Biotech. in Healthcare*, 1(2):167-182.

Agrawal, et al. (1995) "Pharmacokinetics of Antisense Oligonucleotides", *Clin. Pharmacokinet.* 28(1):7-16.

Agrawal (1996) "Preface" In *Methods in Molecular Medicine: Antisense Therapeutics* (Agrawal,ed.) pp. v-vii.

Agrawal, et al. (1998) "Pharmacokinetics and Bioavailability of Antisense Oligonucleotides Following Oral and Colorectal Administrations in Experimental Animals", in *Handbook of Experimental Pharmacology*, vol. 131: Antisense Research and Application, Springer-Verlag, pp. 525-543.

Agrawal (1999) "Importance of Nucleotide Sequence and Chemical Modifications of Antisense Oligonucleotides," *Biochemica et Biophysica Acta* 1489:53-68.

Beaucage (1993) "Oligodeoxyribonucleotides Synthesis" *Methods in Molecular Biology*, vol. 20: Protocols for Oligonucleotides and Analogs, (Agrawal, ed.) Humana Press, Totowa, NJ, pp. 33-61.

Brown (1993) "A Brief History of Oligonucleotide Synthesis" in *Methods in Molecular Biology*, vol. 20: Protocols for Oligonucleotides and Analogs, pp. 1-17.

Craig et al. (1997) "Patent strategies in the antisense oligonucleotide based therapeutic approach" *Exp. Opin. Ther. Patents* 7(10):1175-1182.

*Database CAS Registry* (2003), (Date of entry: 1997), Registry No. 193635-63-1.

Froehler (1993) "Oligodeoxynucleotide Synthesis," *Methods in Molecular Biology*, vol. 20; Protocols for Oligonucleotides and Analogs (Agrawal, ed.) Humana Press, Towtowa, NJ, pp. 63-80.

Furdon (1989) "RNase II cleavage of RNA hybridized to oligonucleotides containing methylphosphonate, phosphorothioate and phosphodiester bonds," *Nucleic Acids Research*, vol. 17;22, pp. 9193-9205.

Galderisi et al. (1999) "Antisense Oligonucleotides as Therapeuitic Agents" *J. Cell. Physiol.* 181:251-257.

Lisziewicz et al. (1992) "Specific Inhibition of Human Immunodeficiency Virus Type 1 Replication by Antisense Oligonucleotides: An *In Vitro* Model for Treatment", *Proc. Natl. Acad. Sci. USA* 89:11209-11213.

Lisziewicz et al. (1993) "Long-Term Treatment of Human Immunodeficiency Virus-Infected Cells with Antisense Oligonucleotide Phosphorothioates", *Proc. Natl. Acad. Sci. USA* 90:3860-3864.

Lisziewicz et al. (1994) "Antisense Oligodeoxynucleotide Phosphorothioate Complementary to Gag mRNA Blocks Replication of Human Immunodeficiency Virus Type 1 in Human Peripheral Blood Cells", *Proc. Natl. Acad. Sci. USA* 91:7942-7946.

Matsukura et al. (1991) "A New Concept in AIDS Treatment: An Antisense Approach and Its Current Status Towards Clinical Application," in *Prospects for Antisense Nucleic Acid Therapy of Cancer and AIDS* (Wickstrom, ed.), Wiley-Liss, Inc., pp. 159-178.

Metelev et al. (1998) "HPLC of Oligodeoxyribonucleoside Phosphorothioates", Abstract No. 151268f, *Chemical Abstracts*, 128(13):272.

Metelev, et al. (1997) "HPLC of Oligodeoxyribonucleoside Phosphorothioates" *Russian Journal of Bioorganic Chemistry*, 23(9):673-677, Translated from Bioorganicheskaya Khimiya 23(9):742-746.

Milligan, et al. (1993) "Current Concepts in Antisense Drug Design", *Journal of Medicinal Chemistry*, 36(14):1923-1937.

Milner et al. (1997) "Selecting Effective Antisense Reagents on Combinatorial Oligonucleotide Arrays," *Nature Biotech.* 15:537-541.

Palu, G., et al. (1999) "In Pursuit of new developments for gene therapy of human diseases," *Journal of Biotechnology*, 68:1-13.

Tamm, I., et al. (Aug. 2001) "Antisense therapy in oncology: new hope for an old idea?" *The Lancet*, 358:489-496.

Uhlmann et al. (1990) "Antisense Oligonucleotides: A New Therapeutic Principle," *Chem. Rev.* 90(4):543-584.

Zamecnik (1996) "History of Antisense Oligonucleotides" in *Methods in Molecular Medicine; Antisense Therapeutics* (Agrawal,ed.) Humana Press, Totowa, NJ, pp. 1-11.

Zhang et al. (1995) "*In Vivo* Stability, Disposition and Metabolism of a "Hybrid" Oligonucleotide Phosphorothioate in Rats," *Biochem. Pharmacol.* 50(4): 545-556.

Zhang et al. (1995) Pharmacokinetics of an Anti-Human Immunodeficiency Virus Antisense Oligodeoxynucleotide Phosphorothioate (GEM 91) in HIV-Infected Subjects, *Clin. Pharmacol. Ther.* 58(1):44-53.

Zhang et al. (1996) "Pharmacokinetics and Tissue Disposition of a Chimeric Oligodeoxynucleoside Phosphorothioate in Rats After Intravenous Administration," *Journal of Pharmacology and Experimental Therapeutics* 278(2):971-979.

Zhao, et al. (2000) "Immunostimulatory Activity of CpG Containing Phosphorothioate Oligodeoxynucleotide is Modulated by Modification of a Single Deoxynucleoside", *Bioorganic & Medicinal Chemistry Letters*, 10:1051-1054.

\* cited by examiner

HIV-SPECIFIC SYNTHETIC OLIGONUCLEOTIDES AND METHODS OF THEIR USE

RELATED APPLICATIONS

This application is a continuation of U.S. Ser. No. 08/914,827, file Aug. 16, 1997 now abandoned, the contents of which are incorporated herein in their entirety.

BACKGROUND OF THE INVENTION

This invention relates to the treatment of HIV infection. More particularly, this invention relates to synthetic modified antisense oligonucleotides and pharmaceutical compositions containing such oligonucleotides and to methods of inhibiting HIV replication and treating HIV infection using such oligonucleotides.

Human immunodeficiency virus types 1 and 2 (HIV-1, HIV-2), formerly called human T-cell leukemia lymphotropic virus-type III (HTLV-III), are believed to be the etiological agents of acquired immune deficiency syndrome (AIDS). HIV is part of the Retroviridaie family, the members of which contain an RNA genome and reverse transcriptase activity. During their growth cycle, retroviruses copy their RNA into proviral DNA. The proviral DNA is able to integrate into the chromosomal DNA of the host cell where it uses the transcriptional and translational machinery of the host to express viral RNA and proteins. Viruses are released from the cell by budding from the cytoplasmic membrane. In the case of HIV-1 and HIV-2, viral replication results in the death of helper T-cell host cells, which leads to a state of severe immunodeficiency, to the development of various malignancies and opportunistic infections, and ultimately to the death of the infected organism.

The incidence of AIDS has risen to epidemic proportions in many countries without the development of preventative treatments or therapies which are successful in the long term. Those few therapeutic agents which have been prescribed, such as the nucleoside analogs 3'-azido-3'-deoxythymidine (AZT), dideoxyinosine (ddI), and dideoxycytosine (ddC), and various protease inhibitors have met with limited success. This has been in part because of the cytotoxicity of these agents. In addition, some viruses escape due to mutations that render them insensitive to these agents and the difficulty of antiviral action due to the ability of the virus to integrate into the host's genome. Thus, there is a long felt need for more effective therapeutic agents and preventative therapies for AIDS.

More recently new chemotherapeutic agents have been developed which are capable of modulating cellular and foreign gene expression. These agents, called antisense oligonucleotides, bind to a target singe-stranded nucleic acid molecules according to the Watson-Crick or the Hoogstein rule of base pairing, and in doing so, disrupt the function of the target by one of several mechanisms: by preventing the binding of factors required for normal translation or transcription; in the case of an mRNA target, by triggering the enzymatic destruction of the message by RNase H; or by destroying the target via reactive groups attached directly to the antisense oligonucleotide.

Antisense oligodeoxynucleotides have been designed to specifically inhibit the expression of HIV-1 and other viruses (see, e.g., Agrawal (1992) *Trends in Biotechnology* 10:152–158; Agrawal et al. in *Gene Regulation: Biology of Antisense RNA and DNA* (Erickson and Izant, eds.) Raven Press Ltd., New York (1992) pp. 273–283); Matsukura et al. in *Prospects for Antisense Nucleic Acid Therapy of Cancer and AIDS,* Wiley-Liss, Inc. (1992) pp. 159–1798); and Agrawal (1991) in *Prospects for Antisense Nucleic Acid Therapy for Cancer and AIDS,* (Wickstron, ed.) Liss, New York, pp. 145–148). For example, it has been shown that antisense oligonucleotides having phosphodiester internucleoside bonds and sequences complementary to portions of genomic HIV-1 RNA inhibit viral replication in early infected cells (Zamecnik et al. (1986) *Proc. Acid. Sci. USA* 83:4143–4147; Goodchild et al. (1988) *Proc. Natl. Acad. Sci USA* 85:5507–5511).

However, these phosphodiester-linked molecules are less able to inhibit viral replication in chronically infected cells (Agrawal et al. (1989) *Proc. Natl. Acad. Sci USA* 86:7790–7794), mainly because of their nuclease susceptibility (Wickstrom (1986) *J. Biochem. Biophys. Meth.* 13:97–102). Therefore, chemically modified, nuclease-resistant analogs have been developed which are effective in inhibiting HIV-1 replication in tissue cultures (see, Sarin et al. (1988) *Proc. Natl Acad. Sci. USA* 85:7448–7451; Agrawal et al. (1988) *Proc. Natl Acad. Sci USA* 85:7079–7083; Matsukura et al. (1988) *Gene* 72:343–347). These analogs include oligonucleotides with nuclease-resistant phosphorothioate internucleotide linkages shown to inhibit HIV-1 replication in both acute infection (U.S. Ser. No. 08/309,823; Agrawal et al. (1989) *Proc. Natl. Acad. Sci USA* 86:7790–7794) and in chronically infected cell lines (Agrawal et al. (1991) in *Gene Regulation: Biology of Antisense RNA,* eds. Erickson et al. (Raven Press, New York), pp. 273–284; Vickers et al. (1991) *Nucleic Acids Res.* 19:3359–3368; Matsukura et al. (1989) *Proc. Natl Acad. Sci.* 86:4244–4248; Agrawal et al. (1988) *Proc. Natl Acad. Sci USA* 85:7079–7083).

However, some phosphorothioate-linked oligonucleotides that have "GC-rich" nucleotide sequences have been found to evoke immunostimmulatory responses in the organisms to whom they have been administered. For example, Kniep et al. (*Nature* (1995) 374:546–549) discloses that oligonucleotides containing the CG dinucleotide flanked by certain other sequences have a mitogenic and other side effects.

Thus, there still remains a need for a more effective anti-HIV oligonucleotide having therapeutic effects that are accompanied by fewer side effects, e.g., little cellular toxicity and reduced immunostimmulatory response.

SUMMARY OF THE INVENTION

It has been discovered that synthetic oligonucleotides directed to a region of the HIV gag inhibit HIV-1 and HIV-2 infection of mammalian cells. These discoveries have been exploited to develop the present invention, which in its broadest aspect, provides synthetic oligonucleotides having a nucleotide sequence specifically complementary to nucleotides 324 to 345 of a conserved gag region of the HIV genome set forth as SEQ ID NO:5. These oligonucleotides have 21 nucleotides ("21mers") which are linked via phosphorothioate internucleotide linkages. Such phosphorothioate linkages contain a substitution of sulfur for oxygen, thereby rendering the oligonucleotide resistant to nucleolytic degradation. The phosphorothioate linkages may be mixed $R_p$ and $S_p$ enantiomers, or they may be stereoregular or substantially stereoregular in either $R_p$ or $S_p$ form (see Iyer et al. (1995) *Tetrahedron Asymmetry* 6:1051 1054).

As used herein, the term "synthetic oligonucleotide" includes chemically synthesized polymers of 12 to 50, preferably from about 15 to about 30, and most preferably, 21 ribonucleotide and/or deoxyribonucleotide monomers connected together or linked by at least one, and preferably more than one, 5' to 3' internucleotide linkage. The term "nucleotide sequence specifically complementary to" nucleotides 324 to 345 of a conserved gag region of the HIV genome is intended to mean a sequence of nucleotides that binds to the gag genomic RNA, proviral DNA, or mRNA sequence under physiological conditions, e.g., by Watson-Crick base pairing (interaction between oligonucleotide and single-stranded nucleic acid) or by Hoogsteen base pairing (interaction between oligonucleotide and double-stranded nucleic acid) or by any other means including in the case of a oligonucleotide binding to RNA, causing pseudoknot formation. Binding by Watson-Crick or Hoogsteen base pairing under physiological conditions is measured as a practical matter by observing interference with the function of the nucleic acid sequence. The term "a conserved gag region" refers to a sequence of nucleotides within the gag gene which is found in related HIV strains.

In one embodiment, the oligonucleotides of the invention comprise at least two 3'-terminal ribonucleotides, at least two 5'-terminal ribonucleotides, or at least two 3'-terminal and at least two 5' terminal ribonucleotides. In preferred embodiments according to this aspect of the invention, the oligonucleotide is a core region hybrid oligonucleotide comprising a region of at least two deoxyribonucleotides, flanked by 5' and 3' ribonucleotide regions, each having at least two ribonucleotides. In one particular embodiment, the oligonucleotides of the invention have four contiguous 3'-terminal ribonucleotides and four contiguous 3'-terminal ribonucleotides, flanking 13 deoxynucleotides.

In preferred embodiments, the ribonucleotides in the hybrid oligonucleotide are 2'-substituted ribonucleotides. For purposes of the invention, the term "2'-substituted" means substitution of the 2' position of the pentose moiety with an —O-lower alkyl group containing one to six saturated or unsaturated carbon atoms, or with an —O-aryl or allyl group having two to six carbon atoms, wherein such alkyl, aryl or allyl group may be unsubstituted or may be substituted, e.g., with halo, hydroxy, trifluoromethyl, cyano, nitro, acyl, acyloxy, alkoxy, carboxyl, carbalkoxyl, or amino groups; or with a hydroxy, an amino or a halo group, but not with a 2'-H group. In specific embodiments, the ribonucleotides are 2'-O-alkyl ribonucleotides such as 2'-O-methyl ribonucleotides.

In particular embodiments, the oligonucleotides of the invention have SEQ ID NO:1, NO:2, NO:3, or NO:4. In some embodiments, these oligonucleotides inhibit HIV-1 or HIV-2 infection in a cell and/or exhibit antiviral activity against HIV-1 and HIV-2.

In yet another aspect, the invention provides pharmaceutical formulations suitable for inhibiting and treating HIV-1 or HIV-2 infection and having reduced side effects such as immunogenicity. These formulations comprise at least one oligonucleotide in accordance with the invention in a pharmaceutically acceptable carrier.

As used herein, a "pharmaceutically or physiologically acceptable carrier" includes any and all solvents (including but not limited to lactose), dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions of the invention is contemplated. Supplementary active ingredients can also be incorporated into the compositions.

In another aspect, the invention provides a method of treating HIV-1 or HIV-2 infection in a mammal. In this method an oligonucleotide according to the invention is administered to the mammal in an amount effective to inhibit the proliferation of the virus. For purposes of the invention, the term "mammal" is meant to encompass primates and humans. In some embodiments, the oligonucleotide is orally administered to the mammal. The term "orally administered" refers to the provision of the formulation via the mouth through ingestion, or via some other part of the gastrointestinal system including the esophagus. In other embodiments, the oligonucleotide is administered via intravenous injection. In yet other embodiments, the oligonucleotide is administered colorectally. The term "colorectal administration" or "rectal administration" or "colorectally administered" refers to the provision of the pharmaceutical formulation of the invention to any part of the large intestine via surgical implantation, anal administration, or any other mode of placement therein.

The invention also provides in another aspect a method of inhibiting HIV-1 or HIV-2 infection in a cell. In this method the cell is contacted with a synthetic oligonucleotide according to the invention.

In yet another aspect, the invention provides a method for introducing an intact oligonucleotide into a mammal. This method comprises administering to the mammal an oligonucleotide according to the invention which is present in intact form in the systemic plasma of the mammal following oral administration. In one embodiment, the oligonucleotide is orally or enterally administered. In another embodiment, the oligonucleotide is intravenously administered.

BRIEF DESCRIPTION OF THE DRAWINGS

The foregoing and other objects of the present invention, the various features thereof, as well as the invention itself may be more fully understood from the following description, when read together with the accompanying drawings in which.

DETAILED DESCRIPTION OF THE PREFERRED EMBODIMENTS

Figure 1:
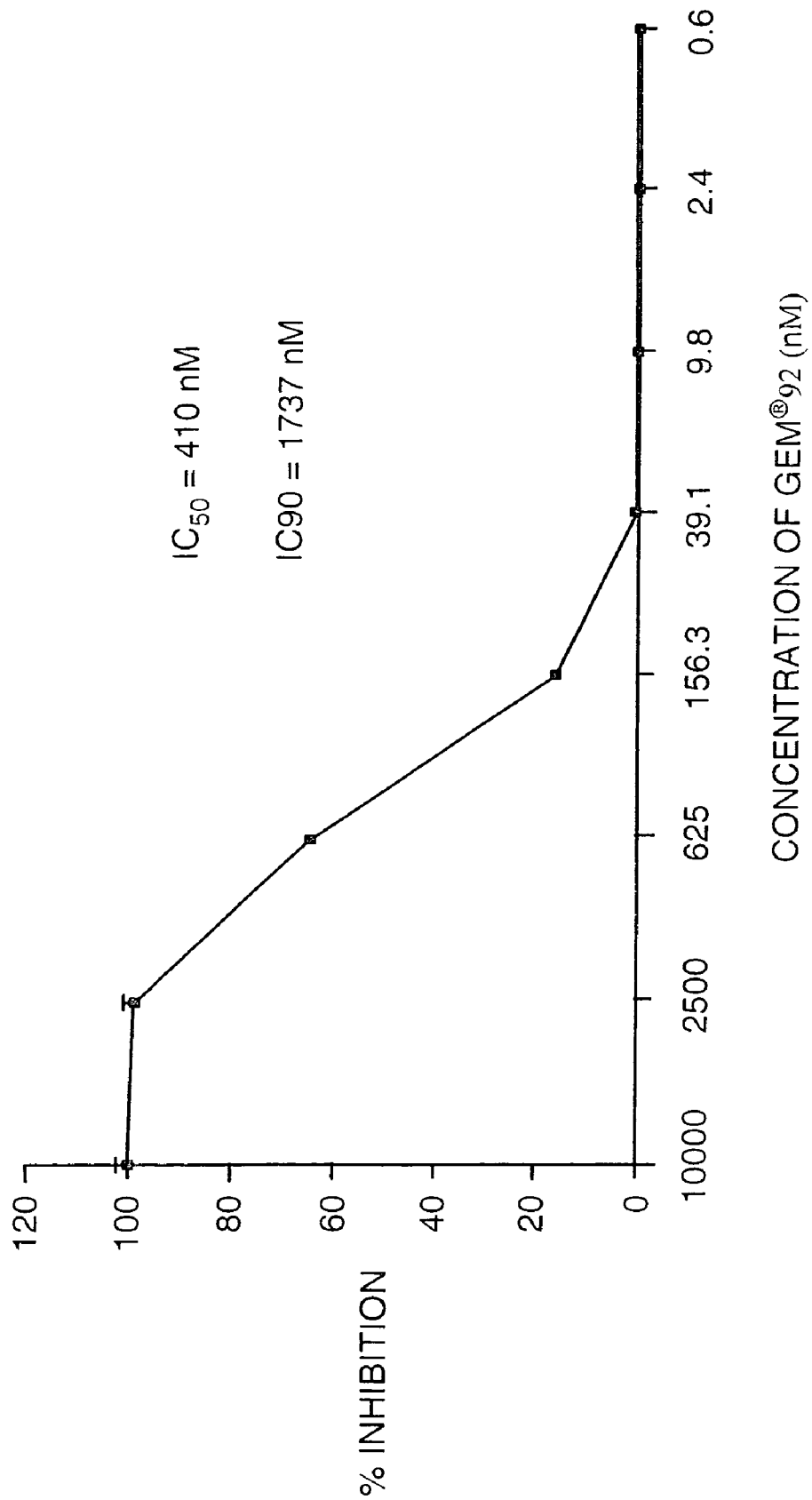
FIG. 1 is a graphic representation of the inhibition of HIV-1 infection in cells treated during initial infection with a 4×4 hybrid oligonucleotide of the invention having SEQ ID NO:1.

The patent and scientific literature referred to herein establishes the knowledge that is available to those with skill in the art. The issued U.S. patents, allowed patent applications, and articles cited herein are hereby incorporated by reference.

It is known that antisense oligonucleotides, can bind to a target single-stranded nucleic acid molecule according to the Watson-Crick or the Hoogsteen rule of base pairing, and in doing so, disrupt the function of the target by one of several mechanisms: by preventing the binding of factors required for normal transcription, splicing, or translation; by triggering the enzymatic destruction of mRNA by RNase H if a contiguous region of deoxyribonucleotides exists in the oligonucleotide, and/or by destroying the target via reactive groups attached directly to the antisense oligonucleotide.

Novel antisense oligonucleotides have been designed which inhibit HIV-1 and HIV-2 replication. These oligonucleotides are synthetic oligonucleotides having phosphorothioate internucleotide linkages and a nucleotide sequence that is complementary to a portion of the gag region of the genome of HIV-1 and HIV-2. Sequences situated in this region have been demonstrated to be essential for viral packaging. These sequences form a stable secondary structure (Harrison et al. (1991) in *RNA Tumor Viruses* (Coffin et al., eds.) Cold Spring Harbor Laboratory, Cold Spring Harbor, N.Y., pp. 235). The oligonucleotides of the invention have been designed to bind to this region of RNA and DNA, thereby disrupting its natural stability and resulting ultimately in the inhibition of viral packaging and translation of gag mRNA. The specific sequence to which the oligonucleotides of the invention are complementary is nucleotides 324–345 of the gag region of HIV-1. This sequence is very conserved among strains of HIV-1, as shown below in TABLE 1.

TABLE 1

| Sequence of: 324–345→ ' | TCTTCCTCTCTCTACCCACGCT CGGAGGCTAGAAGGAGAGAGATGGGTGCGAGAGCGTC AGTA (SEQ ID No:8) | | |
|---|---|---|---|
| Strains of HIV-1 | . . | . . | |
| HTLV/LLAV | G | A | |
| HIVLAI | G | A | |
| HIVNL43 | G | G | |
| HIVMN | G | G | |
| HIVJH3 | G | A | |
| HIVOYI | G | A | |
| HIVCDC4 | G | A | |
| HIVRF | G | A | |
| HIVMAL | G | A (African) | |
| HIVU455 | | A | A CCTCAG (Ugandan) |
| HIVSF2 | (GA) | 4G | G |
| HIVNDK | | C | A |

Targeting an antisense oligonucleotide to such a conserved region including an active gene allows for efficient inhibition of HIV proliferation without the generation of "escape mutants." Escape mutants arise when a mutation occurs in a region of the genome targeted by the antisense oligonucleotide. They occur at a higher frequency in non-coding regions (like the SA region of HIV-1) than in regions encoding a protein.

Oligonucleotides of the invention are more specific, less toxic, and have greater nuclease resistance than many other chemotherapeutic agents designed to inhibit HIV replication. In particular, these oligonucleotide are less immunostimulatory than other oligonucleotides directed to the HIV-1 gag sequence because their nucleotide sequences are not GC-rich. Furthermore, these hybrid oligonucleotides having phosphorthioate linkages are more resistant to nucleolytic degradation than are DNA compounds having solely phosphodiester linkages.

The oligonucleotides useful in the method of the invention are at least 12 nucleotides in length, but are preferably 15 to 21 nucleotides long, with 21mers being most common. They are composed of deoxyribonucleotides, ribonucleotides, or a combination of both (i.e., are "hybrids"), with the 5' end of one nucleotide and the 3' end of another nucleotide being covalently linked by phosphorodithioates or phosphorothioates, non-phosphodiester internucleotide linkages. Oligonucleotides with these linkages can be prepared according to known methods such as phosphoramidate or H-phosphonate chemistry which can be carried out manually or by an automated synthesizer as described by Brown (*A Brief History of Oligonucleotide Synthesis. Protocols for Oligonucleotides and Analogs, Methods in Molecular Biology* (1994) 20:1–8). (See also, e.g., Sonveaux "Protecting Groups in Oligonucleotides Synthesis" in Agrawal (1994) *Method in Molecular Biology* 26:1–72; Uhlmann et al. (1990) *Chem. Rev.* 90:543–583).

The oligonucleotides of the composition may also be additionally modified in a number of ways without compromising their ability to hybridize to the target nucleic acid. Such modifications include, for example, those which are internal or at the end(s) of the oligonucleotide molecule and include additions to the molecule of the internucleoside phosphate linkages, such as cholesteryl or diamine compounds with varying numbers of carbon residues between the amino groups and terminal ribose, deoxyribose and phosphate modifications which cleave, or crosslink to the opposite chains or to associated enzymes or other proteins which bind to the viral genome. Examples of such modified oligonucleotides include oligonucleotides with a modified base and/or sugar such as arabinose instead of ribose, or a 3', 5'-substituted oligonucleotide having a sugar which, at both its 3' and 5' positions is attached to a chemical group other than a hydroxyl group (at its 3' position) and other than a phosphate group (at its 5' position). Other modified oligonucleotides are capped with a nuclease resistance-conferring bulky substituent at their 3' and/or 5' end(s), or have a substitution in one nonbridging oxygen per nucleotide. Such modifications can be at some or all of the internucleoside linkages, as well as at either or both ends of the oligonucleotide and/or in the interior of the molecule. For the preparation of such modified oligonucleotides, see, e.g., Agrawal (1994) *Methods in Molecular Biology* 26; Uhlmann et al. (1990) *Chem. Rev.* 90:543–583). Oligonucleotides which are self-stabilized are also considered to be modified oligonucleotides useful in the methods of the invention (Tang et al. (1993) *Nucleic Acids Res.* 20:2729–2735). These oligonucleotides comprise two regions: a target hybridizing region; and a self-complementary region having an oligonucleotide sequence complementary to a nucleic acid sequence that is within the self-stabilized oligonucleotide.

The preparation of these unmodified and modified oligonucleotides is well known in the art (reviewed in Agrawal et al. (1992) *Trends Biotechnol.* 10:152–158; see, e.g., Uhlmann et al. (1990) *Chem. Rev.* 90:543–584; and (1987) *Tetrahedron. Lett.* 28:(31):3539–3542); Agrawal (1994) *Methods in Molecular Biology* 20:63–80); and Zhang et al. (1996) *J. Pharmacol. Expt. Thera.* 278:1–5).

Preferred oligonucleotides according to the invention are hybrid oligonucleotides in that they contain both deoxyribonucleotides and at least two 2' substituted ribonucleotides at their termin(i/us). For purposes of the invention, the term "2'-substituted" means substitution at the 2' position of the ribose with, e.g., a —O-lower alkyl containing 1–6 carbon atoms, aryl or substituted aryl or allyl having 2–6 carbon atoms e.g., 2'-O-allyl, 2'-O-aryl, 2'-O-alkyl, 2'-halo, or 2'-amino, but not with 2'-H, wherein allyl, aryl, or alkyl groups may be unsubstituted or substituted, e.g., with halo, hydroxy, trifluoromethyl, cyano, nitro, acyl, acyloxy, alkoxy, carboxyl, carbalkoxyl or amino groups. Useful substituted ribonucleotides are 2'-0-alkyls such as 2'-0-methyl, 2'-0-ethyl, and 2'-0-propyl, with 2'-0-methyl being the most preferred.

The hybrid oligonucleotides useful in the method of the invention resist nucleolytic degradation, form stable duplexes with RNA or DNA, and preferably activate RNase H when hybridized with RNA. They may additionally include at least one unsubstituted ribonucleotide. For example, an oligonucleotide useful in the method of the invention may contain all deoxyribonucleotides with the exception of two 2' substituted ribonucleotides at the 3' terminus of the oligonucleotide, or the 5' terminus of the oligonucleotide. Alternatively, the oligonucleotide may have at least two, and preferably 4, substituted ribonucleotides at both its 3' and 5' termini.

Preferred oligonucleotides have at least two and preferably four 2'-0-methyl ribonucleotides at both the 3' and 5' termini, with the remaining nucleotides being deoxyribonucleotides. One preferred oligonucleotide is a 21mer phosphorothioate linked oligonucleotide containing therein deoxyribonucleotides flanked on each side by four 2'-0-methyl ribonucleotides. This preferred oligonucleotide is referred to as a "4×4". One preferred class of oligonucleotides useful in the method of the invention contains four or more deoxyribonucleotides in a contiguous block, so as to provide an activating segment for RNase H. In certain cases, more than one such activating segment will be present at any location within the interior of the oligonucleotide. There may be a majority of deoxyribonucleotides in oligonucleotides according to the invention. In fact, such oligonucleotides may have as many as all but two nucleotide being deoxyribonucleotides.

TABLE 2 lists some representative species of oligonucleotides which are useful in the method of the invention. 2'-substituted nucleotides are underscored.

TABLE 2

| OLIGO NO. | OLIGONUCLEOTIDE (5'→3') | SEQ ID NO: |
|---|---|---|
| 1 | UCGCACCCATCTCTCTCCUUC | 1 |
| 2 | UCGCACCCATCTCTCTCCU_UC_ | 1 |
| 3 | UCGCACCCATCTCTCTCC_UUC_ | 1 |
| 4 | UCGCACCCATCTCTCTC_CUUC_ | 1 |
| 5 | UCGCACCCATCTCTCT_CCUUC_ | 1 |
| 6 | _UCGCA_CCCATCTCTCTCCUUC | 1 |
| 7 | _UCGCA_CCCATCTCTCTCCUUC | 1 |
| 8 | _UCGCA_CCCATCTCTCTCCUUC | 1 |
| 9 | _UCGCA_CCCATCTCTCTCCUUC | 1 |
| 10 | _UCGCA_CCCATCTCTCTCCU_UC_ | 1 |
| 11 | _UCGCA_CCCATCTCTCTCC_UUC_ | 1 |
| 12 | _UCGCA_CCCATCTCTCTCC_UUC_ | 1 |
| 13 | _UCGCA_CCCATCTCTCTC_CUUC_ | 1 |
| 14 | _UCGC_ACCCATCTCTCTCC_UUC_ | 1 |
| 15 | _UCGC_ACCCATCTCTCTCCU_UC_ | 1 |
| 16 | _UCGC_ACCCATCTCTCTCC_UUC_ | 1 |
| 17 | _UCG_CACCCATCTCTCTC_CUUC_ | 1 |
| 18 | _UCG_CACCCATCTCTCTCC_UUC_ | 1 |
| 19 | _UCG_CACCCATCTCTCTC_CUUC_ | 1 |
| 20 | TCGCACCCATCTCTCTCCTTC | 2 |
| 21 | CGCACCCATCTCTCTCCUUCU | 3 |
| 22 | CGCACCCATCTCTCTCCUU_CU_ | 3 |
| 23 | CGCACCCATCTCTCTCCU_UCU_ | 3 |
| 24 | CGCACCCATCTCTCTCCU_UCU_ | 3 |
| 25 | CGCACCCATCTCTCTC_CUUCU_ | 3 |
| 26 | _CG_CACCCATCTCTCTCCUUCU | 3 |
| 27 | _CGC_ACCCATCTCTCTCCUUCU | 3 |
| 28 | _CGCA_CCCATCTCTCTCCUUCU | 3 |
| 29 | _CGCAC_CCATCTCTCTCCUUCU | 3 |
| 30 | _CGCAC_CCATCTCTCTCCUU_CU_ | 3 |
| 31 | _CGCAC_CCATCTCTCTCCU_UCU_ | 3 |
| 32 | _CGCA_CCCATCTCTCTCCU_UCU_ | 3 |
| 33 | _CGCAC_CCATCTCTCTC_CUUCU_ | 3 |
| 34 | _CGCA_CCCATCTCTCTCCU_UCU_ | 3 |
| 35 | _CGCA_CCCATCTCTCTCCUU_CU_ | 3 |
| 36 | _CGCA_CCCATCTCTCTCCUU_CU_ | 3 |
| 37 | _CGCA_CCCATCTCTCTCC_UUCU_ | 3 |
| 38 | _CGCA_CCCATCTCTCTCCU_UCU_ | 3 |
| 39 | _CGCA_CCCATCTCTCTCC_UUCU_ | 3 |
| 40 | CGCACCCATCTCTCTCCTTCT | 4 |

Oligonucleotides as described above are useful in a method of inhibiting HIV-1 or HIV-2 infection in a cell. In this method a cell is contacted with an oligonucleotide of the invention such that virus present in the cell at the time of contact, or after such contact is unable to replicate.

Figure 2:
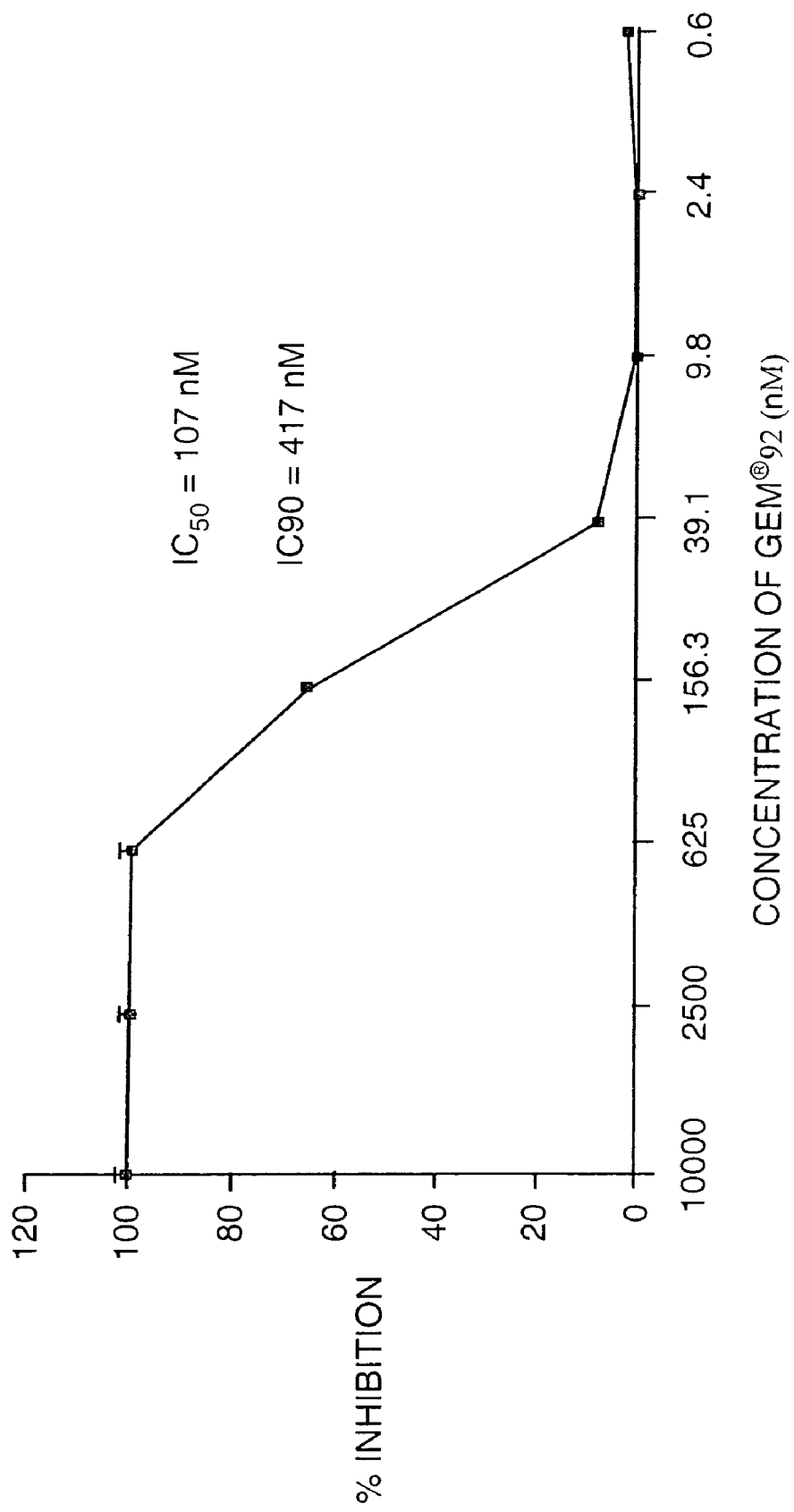
FIG. 2 is a graphic representation of the inhibition of HIV-1 infection in cells treated following initial infection with a 4×4 hybrid oligonucleotide of the invention having SEQ ID NO:1.

To determine whether oligonucleotides of the invention could inhibit or prevent HIV infection, cytopathic effect-(CPE-)based infection experiments were performed in MT-4 cells. The results of these studies indicate that oligonucleotides of the invention can both inhibit an existing infection (FIG. 1) and protect against such infection (FIG. 2).

In addition, it was determined that synthetic oligonucleotides systemically administered to pregnant murine females crossed the placenta and became available in the blood of embryos in utero. Thus, it is contemplated that oligonucleotides of the invention will be used in a method of treating the fetuses and human mothers harboring HIV.

The oligonucleotides described herein are administered to the mammal in the form of therapeutic pharmaceutical formulations that are effective for treating virus infection. These pharmaceutical formulations may be administered in conjunction with other therapeutic agents, e.g., AZT and/or various protease inhibitors, to treat AIDS.

The therapeutic pharmaceutical formulation containing at least one oligonucleotide according to the invention includes a physiologically acceptable carrier which is congruent with the mode of administration. Examples include an inert diluent or an assimilable edible carrier. Suitable formulations that include pharmaceutically acceptable excipients for introducing compounds to the bloodstream by intravenous injection and other than injection routes can be found in *Remington's Pharmaceutical Sciences* (18th ed.) (Genarro, ed. (1990) Mack Publishing Co., Easton, Pa.).

The pharmaceutical forms suitable for injectable use include sterile aqueous solutions or dispersions and sterile powders for the extemporaneous preparation of sterile injectable solutions or dispersions. In all cases the form must be sterile. It must be stable under the conditions of manufacture and storage and may be preserved against the contaminating action of microorganisms, such as bacterial and fungi. The carrier can be a solvent or dispersion medium. The prevention of the action of microorganisms can be brought about by various antibacterial and antifungal agents. Prolonged absorption of the injectable therapeutic agents can be brought about by the use of the compositions of agents delaying absorption. Sterile injectable solutions are prepared by incorporating the oligonucleotide in the required amount in the appropriate solvent, followed by filtered sterilization.

Alternatively, the oligonucleotide of the invention and other ingredients may be enclosed in a hard or soft shell gelatin capsule, compressed into tablets, or incorporated directly into the individual's diet. The oligonucleotide may be incorporated with excipients and used in the form of ingestible tablets, buccal tablets, troches, capsules, elixirs, suspensions, syrups, wafers, and the like. When the oligonucleotide is administered orally, it may be mixed with other food forms and pharmaceutically acceptable flavor enhancers. When the oligonucleotide is administered enterally, they may be introduced in a solid, semi-solid, suspension, or emulsion form and may be compounded with any number of well-known, pharmaceutically acceptable additives. Sustained release oral delivery systems and/or enteric coatings for orally administered dosage forms are also contemplated such as those described in U.S. Pat. Nos. 4,704,295, 4,556,552, 4,309,404, and 4,309,406.

As used herein, the term "therapeutically effective amount" means the total amount of each active component of the pharmaceutical formulation or method that is sufficient to show a meaningful subject or patient benefit, i.e., a reduction in tumor growth or in the expression of proteins which cause or characterize the cancer. When applied to an individual active ingredient, administered alone, the term refers to that ingredient alone. When applied to a combination, the term refers to combined amounts of the active ingredients that result in the therapeutic effect, whether administered in combination, serially or simultaneously.

A "therapeutically effective manner" refers to a route, duration, and frequency of administration of the pharmaceutical formulation which ultimately results in meaningful patient benefit, as described above. In some embodiments of the invention, the pharmaceutical formulation is administered via injection, sublingually, colorectally, intradermally, orally, enterally or in bolus, continuous, intermittent, or continuous, followed by intermittent regimens.

The therapeutically effective amount of synthetic oligonucleotide administered in the method of the invention will depend upon the nature and severity of the condition being treated, and on the nature of prior treatments which the patent has undergone. Ultimately, the attending physician will decide the amount of synthetic oligonucleotide with which to treat each individual patient. Initially, the attending physician may administer low doses of the synthetic oligonucleotide and observe the patient's response. Larger doses of synthetic oligonucleotide may be administered until the optimal therapeutic effect is obtained for the patient, and at that point the dosage is not increased further. It is contemplated that the dosages of the pharmaceutical compositions administered in the method of the present invention should contain about 0.1 to 100.0 mg/kg body weight per day, preferably 0.1 to 75.0 mg/kg body weight per day, more preferably, 1.0 to 50.0 mg/kg body weight per day, even more preferably, 1 to 25 mg/kg body weight per day, and even more preferably, 1 to 10 or 1 to 5.0 mg/kg body weight per day. The oligonucleotide is preferably administered at a sufficient dosage to attain a blood level of oligonucleotide from about 0.01 $\mu M$ to about 100 $\mu M$. Preferably, the concentration of oligonucleotide at the site of aberrant gene expression should be from about 0.01 $\mu M$ to about 50 $\mu M$, more preferably, from about 0.01 $\mu M$ to about 10 $\mu M$, and most preferably from about 0.05 $\mu M$ to about 5 $\mu M$. However, for localized administration, much lower concentrations than this may be effective, and much higher concentrations may be tolerated. It may be desirable to administer simultaneously or sequentially a therapeutically effective amount of one or more of the therapeutic compositions of the invention when individual as a single treatment episode.

It will be appreciated that the unit content of active ingredient or ingredients contained in an individual dose of each dosage form need not in itself constitute an effective amount since the necessary effective amount can be reached by administration of a plurality of dosage units (such as suppositories, gels, or creams, or combinations thereof). In fact, multi-dosing (once a day) has been shown to significantly increase the plasma and tissue concentrations of MBO's (data not shown).

Administration of pharmaceutical compositions in accordance with the invention or to practice the method of the present invention can be carried out in a variety of conventional ways, such as by oral ingestion, enteral, colorectal, or transdermal administration, inhalation, sublingual administration, or cutaneous, subcutaneous, intramuscular, intraocular, intraperitoneal, or intravenous injection, or any other route of administration known in the art for administrating therapeutic agents.

When the composition is to be administered orally, sublingually, or by any non-injectable route, the therapeutic formulation will preferably include a physiologically acceptable carrier, such as an inert diluent or an assimilable edible carrier with which the composition is administered. Suitable formulations that include pharmaceutically acceptable excipients for introducing compounds to the bloodstream by other than injection routes can be found in *Remington's Pharmaceutical Sciences* (18th ed.) (Genarro, ed. (1990) Mack Publishing Co., Easton, Pa.). The oligonucleotide and other ingredients may be enclosed in a hard or soft shell gelatin capsule, compressed into tablets, or incorporated directly into the individual's diet. The therapeutic compositions may be incorporated with excipients and used in the form of ingestible tablets, buccal tablets, troches, capsules, elixirs, suspensions, syrups, wafers, and the like. When the therapeutic composition is administered orally, it may be mixed with other food forms and pharmaceutically acceptable flavor enhancers. When the therapeutic composition is administered enterally, they may be introduced in a solid, semi-solid, suspension, or emulsion form and may be compounded with any number of well-known, pharmaceutically acceptable additives. Sustained release oral, delivery systems and/or enteric coatings for orally administered dosage forms are also contemplated such as those described in U.S. Pat. Nos. 4,704,295, 4,556,552, 4,309,404, and 4,309,406.

When a therapeutically effective amount of composition of the invention is administered by injection, the synthetic oligonucleotide will preferably be in the form of a pyrogen free, parenterally acceptable, aqueous solution. The preparation of such parenterally acceptable solutions, having due regard to pH, isotonicity, stability, and the like, is within the skill in the art. A preferred pharmaceutical composition for injection should contain, in addition to the synthetic oligonucleotide, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art. The pharmaceutical formulation can be administered in bolus, continuous, or intermittent dosages, or in a combination of continuous and intermittent dosages, as determined by the physician and the degree and/or stage of illness of the patient. The duration of therapy using the pharmaceutical composition of the present invention will vary, depending on the unique characteristics of the oligonucleotide and the particular therapeutic effect to be achieved, the limitations inherent in the art of preparing such a therapeutic formulation for the treatment of humans, the severity of the disease being treated and the condition and potential idiosyncratic response of each individual patient. Ultimately the attending physician will decide on the appropriate duration of intravenous therapy using the pharmaceutical composition of the present invention.

To determine the preclinical range of anti-HIV activity of various oligonucleotides of the invention (see TABLE 2), evaluations were performed with Oligo 12 (having SEQ ID NO:1), Oligo 32 (SEQ ID NO:3) and Oligo 41 (SEQ ID NO:6). These evaluations were performed to determine the activity of these compounds against a variety of wild type and drug resistant strains of HIV 1, including both laboratory derived and low passage, clinical strains of virus and T lymphocyte tropic and monocyte macrophage tropic viruses such as those listed below in TABLE 3.

TABLE 3

BIOLOGICAL PROPERTIES OF CLINICAL STRAINS OF HIV-1

| ISOLATE | TROPISM | AZT IC$_{50}$ (μM) | ddi IC$_{50}$ (μM) | SYNCYTIA | GROWTH |
|---|---|---|---|---|---|
| BAKI | L | 0.049 | 2.61 | SI | R/H |
| SLKA | M | 0.025 | 0.32 | NSI | S/L |
| WEJO | L | 0.056 | 2.18 | SI | R/H |
| ROJO | L | 0.016 | 0.87 | SI | R/H |
| ROMA | M | 0.016 | 0.16 | SI | R/H |
| STDA | L | 0.017 | 0.23 | SI | R/H |

TABLE 3-continued

BIOLOGICAL PROPERTIES OF CLINICAL STRAINS OF HIV-1

| ISOLATE | TROPISM | AZT IC$_{50}$ (μM) | ddi IC$_{50}$ (μM) | SYNCYTIA | GROWTH |
|---|---|---|---|---|---|
| WOME | L | 0.016 | 0.41 | SI | R/H |
| VIHU | L | 0.016 | 1.21 | NSI | S/L |
| TEKI | L | 0.029 | 0.37 | NSI | S/L |
| TEKI | M | 0.016 | 1.70 | NSI | S/L |
| DEJO | L | 0.015 | ND | NSI | S/L |
| BLCH | L | 0.010 | ND | NSI | S/L |
| RIARL | L | 0.010 | ND | NSI | S/L |

L - lymphocyte
M - macrophage
SI - syncytium inducing
NSI - non-syncytium inducing
R/H - rapid/high
S/L - slow/low In addition, the activity of the compounds was evaluated against HIV-2, and the toxicity of Oligo 41 was evaluated by a variety of methods in infected and uninfected, established and fresh human cells.

Figure 3:
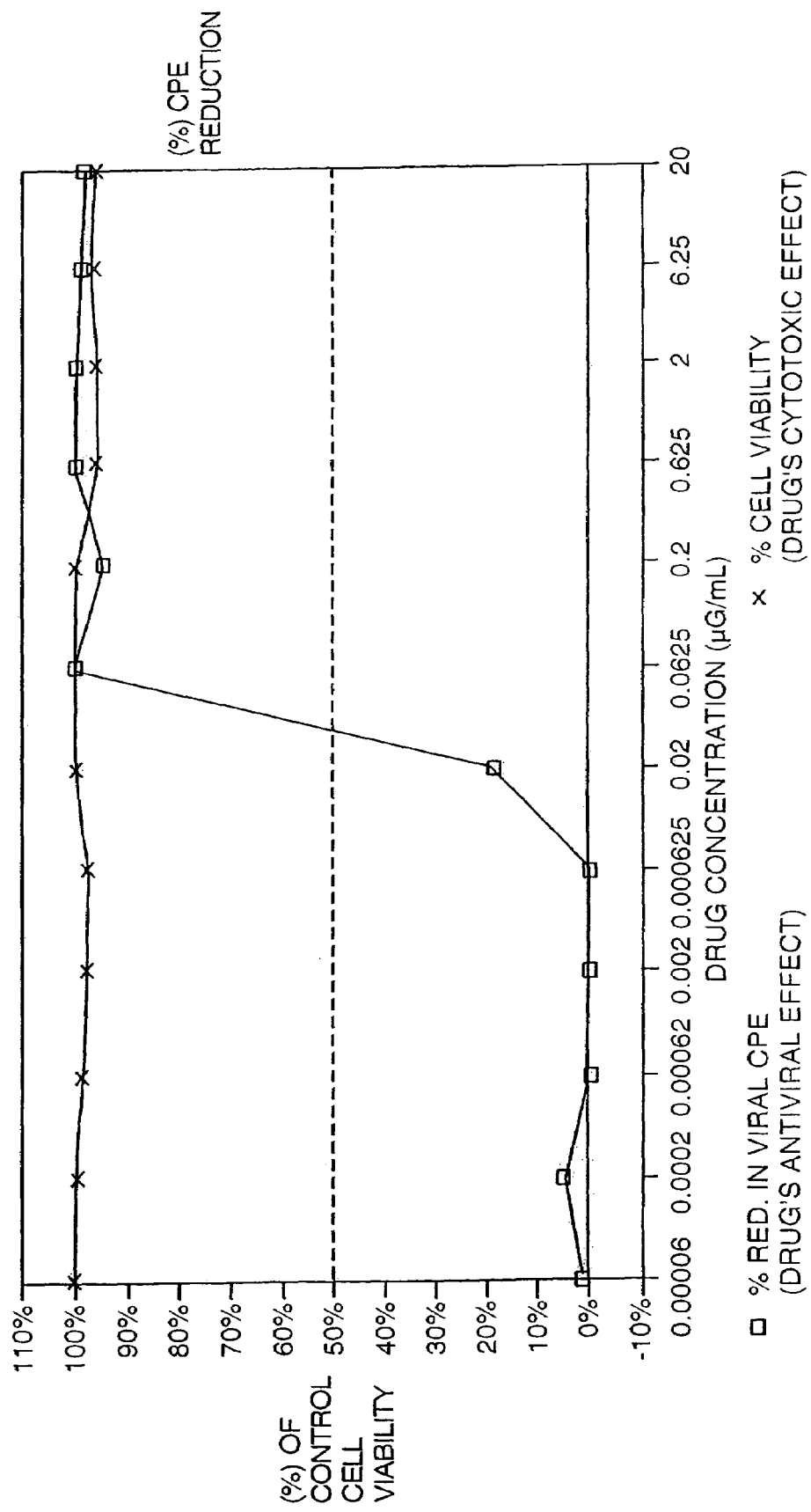
FIG. 3 is a graphic representation of the results of an XTT assay demonstrating the ability of a 4×4 oligonucleotide of the invention having SEQ ID NO:1 to inhibit HIV-2-induced cell killing.

The initial experiment performed involved evaluation of Oligos 12, 32, and 41 against three laboratory strains of HIV-1 (IIIB, RF and SK1) and one strain of HIV-2 (ROD) in parallel with the positive control compound ddC in the XTT-based anti-HIV assay. All these oligonucleotides are active against both HIV-1 and HIV-2. An enhanced level of activity was detected with these compounds when evaluated against the HIV-2 strain ROD. Representative results are shown in FIG. 3.

In another experiment, the anti-HIV activity of Oligos 12, 32, and 41 was evaluated against a variety of low passage, clinical strains of HIV-1 in fresh human peripheral blood mononuclear cells. These strains include viruses obtained from pediatric patients attending the Children's Hospital University of Alabama at Birmingham as well as viruses representative of the various HIV-1 clades found throughout the world, shown below in TABLE 4.

TABLE 4

BIOLOGICAL PROPERTIES OF CLADE VIRUS ISOLATES

| VIRUS | CLADE | PHENOTYPE | COUNTRY |
|---|---|---|---|
| 92RWOO9A | A | NSI | Rwanda |
| 92UG029A | A | SI | Uganda |
| 92BR021B | B | SI | Brazil |
| 92TH026B | B | NSI | Thailand |
| 92BR025C | C | NSI | Brazil |
| 92UG021D | D | SI | Uganda |
| 92UG035D | D | NSI | Uganda |
| 92TH022E | E | NSI | Thailand |
| 93BR029F | F | NSI | Brazil |
| 93BR020F | F | SI | Brazil |

In addition to these T-tropic strains, the activity of the compounds was also evaluated against the monocyte-macrophage strains BaL and ADA. Oligos 12 and 32 according to the invention, as well as Oligo 41 are active against low passage clinical T-tropic strains of HIV-1. The activity of the compounds varies from strain to strain. The compounds were not active against the monocyte-macrophage-tropic strains BaL and ADA.

In other studies, the anti-HIV activity of Oligos 12, 32, and 41 was evaluated against a variety of drug-resistant virus strains, including viruses resistant to nevirapine (N119), 3TC (M198I), protease inhibitors (JE105/R and KN1272/R) and AZT (4×AZT-R).

The results of these evaluations indicate that these oligonucleotides remained active against viruses resistant to nevirapine, 3TC and the protease inhibitors, but were less active against viruses with mutations conferring resistance to AZT. An enhanced level of activity was detected against the nevirapine-resistant strain N119.

In yet another experiment, the toxicity of Oligo 41 was evaluated in uninfected and HIV-1 infected fresh human peripheral blood mononuclear cells, using a variety of quantitative endpoints. Toxicity was evaluated using the tetrazolium dyes XTT or MTT, trypan blue cell and cell viability counting and the incorporation of tritiated thymidine. Two replicate assays were performed. In the first assay, Oligo 41 was used at a high test concentration of 50 µg/ml and toxicity was evaluated on day 7. No toxicity was detected by any of the quantitative endpoints employed. A second assay was performed to further evaluate toxicity at higher compound concentration and with longer exposure to the compound. In this assay, employing a high test concentration of 150 µg/ml and extending the time of drug exposure from 7 days until 14 days, once again no toxicity was detected.

In another set of experiments, the bioavailability of Oligo 12 was examined in vivo and was found to be intravenously and orally bioavailable to rats and monkeys after a single dose.

In addition, synthetic oligonucleotides systemically administered to pregnant murine females were found to cross the placenta and be available in the blood of embryos in utero. Thus, it is contemplated that oligonucleotides of the invention be used in methods of treating human fetuses and mothers harboring HIV.

In order to determine if the oligonucleotide of the invention administered according to the method of the invention is absorbed into body tissues, and if so, in which tissues absorption occurs, the following study was performed. Samples of various body tissues from treated monkeys and rats were analyzed for radioactivity at increasing hours after intravenous or oral administration of a radioactively labelled oligonucleotide specific for HIV. This oligonucleotide was found to be absorbed through the gastrointestinal tract and accumulated in various organs and tissues.

To evaluate the chemical form of radioactivity in plasma HPLC is used to demonstrate the presence of both intact oligonucleotide as well as metabolites various hours after oral administration. Intact oligonucleotide may also be detected in liver various hours after administration. Further evidence to support the absorption of the oligonucleotide may come from urine sample analysis after radioactively labelled gag-specific oligonucleotide was orally administered. That the oligonucleotide continues to be excreted in the urine over time following the administration of radiolabelled oligonucleotide implies that other tissues had absorbed it, and that the body was capable of absorption for an extended period of time.

The following examples illustrate the preferred modes of making and practicing the present invention, but are not meant to limit the scope of the invention since alternative methods may be utilized to obtain similar results.

EXAMPLE 1

Synthesis and Purification of Oligonucleotides

Oligonucleotide phosphorothioates were synthesized using an automated DNA synthesizer (Model 8700, Biosearch, Bedford, Mass.) using a beta-cyanoethyl phosphoramidate approach on a 10 micromole scale. To generate the phosphorothioate linkages, the intermediate phosphite linkage obtained after each coupling was oxidized using 3H, 1,2-benzodithiole-3H-one-1,1-dioxide (see Beaucage, in *Protocols for Oligonucleotides and Analogs: Synthesis and Properties,* Agrawal (ed.), (1993) Humana Press, Totowa, N.J., pp. 33–62).

Hybrid oligonucleotides were synthesized similarly, except that segments containing 2'-O-methylribonucleotides were assembled using 2'-O-methylribonucleoside phosphoramidite, followed by oxidation to a phosphorothioate or phosphodiester linkage as described above. Deprotection and purification of oligonucleotides was carried out according to standard procedures, (see Padmapriya et al. (1994) *Antisense Res. & Dev.* 4:185–199).

EXAMPLE 2

Propacation and Ouantitation of Cell Lines and Virus Stocks

A. Cells

The CEM-SS cell line (Southern Research Institute-Frederick Research Center, Frederick, Md.) is highly susceptible to infection with HIV, rapidly form multinucleated syncytia, and are eventually killed by HIV. The cells were maintained ($2-7 \times 10^5$ cells per ml) in RPMI 1640 tissue culture medium supplemented with 10% fetal bovine serum, glutamine, and antibiotics, and were passaged twice weekly at 1:20 dilution. Passage number was logged each week. Cells were discarded after twenty weeks of passage and fresh CEM-SS cells thawed and utilized in the assay. Stocks of CEM-SS cells were frozen in liquid nitrogen in 1 ml NUNC vials in 90% fetal calf serum and 10% dimethyl sulfoxide (DMSO). Following thawing, CEM-SS cells were routinely ready to be utilized in the primary screen assay after two weeks in culture. Prior to replacing a late passage cell line, the new CEM-SS cells were tested in the screening assay protocol utilizing the current stock of infectious virus and AZT. If the infectivity of the virus was significantly different on the new cells or if AZT appeared less active than expected the new cells were not entered into the screening program. Mycoplasma testing was routinely performed on all cell lines.

Other viral isolates tested included the following drug resistant strains.

The N119 isolate was derived in vitro by culture of the clinical strain A018 in the presence of the nonnucleoside reverse transcriptase inhibitor nevirapine. This isolate was obtained from the NIAID AIDS research and Reference Reagent Program (catalog #1392). The isolate possesses one mutation in the reverse transcriptase (Y181C) and we have found the isolate to be extremely cytopathic to T cells such as CEM-SS and MT2 (Richman et al. (1991) *Proc. Natl. Acad. Sci. USA* 88:11241). The 3TC/M1841 isolate was selected in vitro using the wild type IIIB strain of virus and sequential passage of the virus in the presence of increasing drug concentration in CEM-SS cells (Buckheit Jr. et al. (1996) *Antimicrob. Chem. Chemother.* 7:243–252). The JE 105/R isolate was derived from sequential passage of IIIB in the presence of a protease inhibitor. This isolate possesses the I84V and S37N amino acid changes in the protease. The KNI272/R isolate was derived from sequential passage bf IIIB in the presence of the protease inhibitor KNI 272. The isolate possesses three amino acid changes in the protease, F53L, A71V and T80I. The 4×AZT-Ri isolate was obtained by site-directed mutagenesis through introduction of four amino acid changes in the reverse transcriptase of the NL4-3 wild type virus. The four amino acid changes are D67N, K70R, T215Y, and K219Q.

B. Virus

Virus pools (Southern Research Institute-Frederick Research Center, Frederick M) were prepared and titrated in CEM-SS cells, placed in 5 ml aliquots, and frozen at −135° C. After thawing, unused virus is discarded to avoid changes in infectious titer. Virus pools were prepared by the acute infection of $5\times10^5$ CEM-SS cells with HIV in a volume of 200 µl at a multiplicity of infection determined to give complete cell killing at day 7 post-infection (approximately 0.05 for the $III_B$ isolate of HIV-1 and 0.01 for the RF isolate of HIV-1).

C. Assay

Infection was allowed to proceed for one hour at 37° C., after which the cells were transferred to a T25 flask and the volume increased to 2 ml. On day 1 post-infection the volume was brought to 5 ml and on day 2 the volume was increased to 10 ml. Beginning on day 4, the cells were pelleted, the supernatant saved, and the cells resuspended in a fresh 10 ml aliquot of tissue culture medium. Complete medium changes on a daily basis, rather than allowing growth of the cells in the medium for longer periods of time, allowed the virus inoculum utilized in the primary screen to remain relatively undepleted of nutrients when it is used to infect cells. The staining reaction utilized (XTT, see method below) required that the glucose concentration remain high (161). Wells depleted of glucose by cell growth will not permit metabolic conversion of the tetrazolium dye to the formazan product.

Cell-free supernatants from the acutely infected cells were saved on day 4, day 5, day 6, and day 7. An aliquot of supernatant was saved separately on each day for use in titer determination. Titer determinations included reverse transcriptase activity assay (see below), endpoint titration or plaque assay (CEM-SS) quantification of infectious particles (see below), and quantification of cell killing kinetics.

It has been determined that peak levels of infectious virus are produced in the acutely infected cultures as the viability of the cells falls through the 50% level. Since the primary screening assay quantifies the protective effects of a compound by its ability to inhibit HIV-induced cytopathic effects, the quantity of virus required to kill CEM-SS cells in 6 days was routinely utilized to determine the amount of virus required per well in the primary screening assay. Each of the daily pools was titrated in the primary screening tetrazolium dye XTT assay protocol (see below) by performing two-fold dilutions of the virus beginning at a high test concentration of 50 µl of virus per well. The XTT staining method was utilized to determine the exact amount of virus required to kill all of the CEM-SS cells in each well and this minimum amount of virus was utilized for performance of all primary testing. Identical methods were utilized to prepare all virus isolates utilized, including laboratory-derived strains of HIV-1, HIV-2 and SIV. Clinical isolates utilized were passaged in fresh human cells. The methods for the growth of these cells and the production of virus pools is described below.

EXAMPLE 3

Microtiter Antiviral XTT Assay

A. Cell Preparation:

CEM-SS sells (AIDS Research and Reference Reagent Program, NIH) or other established human T cell lines used in these experiments were passaged in T-150 flasks for use in the assay. On the day preceding the assay, the cells were split 1:2 to assure they would be in an exponential growth phase at time of infection. On the day of assay the cells were washed twice with tissue culture medium and resuspended in fresh tissue cultures medium. Total cell and viability counting was performed using a hemacytometer and trypan blue dye exclusion. Cell viability was greater than 95% for the cells to be utilized in the assay. The cells were pelleted and resuspended at $2.5\times10^4$ cells per ml in tissue culture medium. Cells were added to the drug-containing plates in a volume of 50 µl.

B. Virus Preparation

A pretitered aliquot of virus was removed from the freezer −80° C.) and allowed to thaw slowly to room temperature in a biological safety cabinet. The virus was resuspended and diluted into tissue culture medium such that the amount of virus added to each well in a volume of 50 µl will be the amount determined to give complete cell killing at 6 days post-infection. In general the virus pools produced with the IIIB isolate of HIV required the addition of 5 µl of virus per well. Pools of RF virus were five to ten-fold more potent, requiring 0.5 to 1 µl per well. $TCID_{50}$ calculation by endpoint titration in CEM-SS cells indicated that the multiplicity of infection of these assays ranged from 0.005 to 2.5.

C. Plate Format

Each plate contained cell control wells (cells only), virus control wells (cells plus virus), drug toxicity control wells (cells plus drug only), drug colorimetric control wells (drug only) as well as experimental wells (drug plus cells plus virus).

D. XTT Staining of Screening Plates

After 6 days of incubation at 37° C. in a 5% $CO_2$ incubator, the test plates were analyzed by staining with the tetrazolium dye XTT. XTT-tetrazolium is metabolized by the mitochondrial enzymes of metabolically active cells to a soluble formazan product, allowing the rapid quantitative analysis of the inhibition of HIV-induced cell killing by anti-HIV test substances. On day 6 post-infection plates were removed from the incubator and observed. The use of round bottom microtiter plates allows rapid macroscopic analysis of the activity of a given test compound by the evaluation of pellet size. The results of the macroscopic observations were confirmed and enhanced by further microscopic analysis.

XTT solution was prepared daily as a stock of 1 mg/ml in PBS. Phenazine methosulfate (PMS) solution was prepared at 15 mg/ml in PBS and stored in the dark at −20° C. XTT/PMS stock was prepared immediately before use by diluting the PMS 1:100 into PBS and adding 40 µl per ml of XTT solution. Fifty microliters of XTT/PMS was added to each well of the plate and the plate was incubated for an additional 4 hours at 37° C. Adhesive plate sealers were used in place of the lids, the sealed plate was inverted several times to mix the soluble formazan product and the plate was read spectrophotometrically at A450 nm with a Molecular Devices Vmax plate reader. Using an in-house computer program % CPE (cytopathic effect) reduction, % cell viability, $IC_{25, 50\ \&\ 95}$, $TC_{25, 50\ \&\ 95}$ and other indices were calculated and the graphic results summary was displayed.

EXAMPLE 4

Reverse Transcriptase Activity Assay

A microtiter based reverse transcriptase (RT) reaction was utilized (Buckheit et al (1991) *AIDS Research and Human Retroviruses* 7:295–302). Tritiated thymidine triphosphate (NEN) (TTP) was resuspended in distilled $H_2O$ at 5 Ci/ml. Poly rA and oligo dT were prepared as a stock solution which was kept at −20° C. The RT reaction buffer was prepared fresh on a daily basis and consists of 125 µl 1 M EGTA, 125 µl dH$_2$O, 125 µl Triton X-100, 50 µl 1 M Tris (pH 7.4), 50 µl 1 M DTT, and 40 µl 1 M MgCl$_2$. These three solutions were mixed together in a ratio of one part distilled water. Ten microliters of this reaction mixture was placed in a round bottom microtiter plate and 15 µl of virus containing supernatant was added and mixed. The plate was incubated at 37° C. and incubated for 60 minutes. Following reaction, the reaction volume was spotted onto filter mats, washed 6 times for 5 minutes each in a 5% sodium phosphate buffer, two times for 1 minute each in distilled water, two times for 1 minute each in 70% ethanol, and then dried. The dried filter mat was placed in a plastic sample bag, Betaplate scintillation fluid was added and the bag was heat-sealed. Incorporated radioactivity was quantified utilizing a Wallac Microbeta, scintillation counter (Gaithersburg, Md.).

EXAMPLE 5 p24 ELISA

ELISA kits were purchased from Coulter (Miami, Fla.). The assay is performed according to the manufacturer's recommendations. Prior to ELISA analysis the reverse transcriptase activity assays (described above) were routinely performed and used the values for incorporated radioactivity in the RT activity assay to determine the dilution of our samples requires for the ELISA. Standard curves were constructed so that the dilutions of virus to be used in the p24 ELISA could be accurately determined from the RT activity assay. Control curves were generated in each assay to accurately quantify the amount of capsid protein in each sample. Data was obtained by spectrophotometric analysis at 450 nm using a plate reader. Molecular Devices Vmax P24 (Sunnydale, Calif.) concentrations were calculated from the optical density values by use of the Molecular Devices (San Hose, Calif.) software package Soft Max.

EXAMPLE 6

Infectious Particles

Infectious virus particles were qualified utilizing the CEM-SS plaque assay as described by Nara et al. (*Nature* (1988) 332:469–470). Flat bottom 96-well microtiter plates were coated with 50 µl of poly-L-lysine (Sigma. St. Louis, Mo.) at 50 µg/ml for 2 hours at 37° C. The wells were then washed with PBS and 2.5×10$^5$ CEM-SS cells were placed in the microtiter well where they became fixed to the bottom of the plate. Enough cells were added to form a monolayer of CEM-SS cells in each well. Virus containing supernatant was added from each well of the XTT plate, including virus and cell controls and each serial dilution of the test substance. The number of syncytia were qualified in the flat-bottom 96-well microtiter plate with an Olympus CK2 inverted microscope at 4 days following infection. Each syncytium resulted from a single infectious HIV virion.

EXAMPLE 7

Anti-HIV Activity in Fresh Human Cells

A. Assay in Fresh Human T-Lymphocytes

Fresh human peripheral blood lymphocytes (PBL) were isolated from voluntary Red Cross donors, seronegative for HIV and HBV. Leukophoresed blood was diluted 1:1 with Dulbecco's phosphate buffered saline (PBS), layered over 14 ml of Ficoll-Hypaque density gradient in a 50 ml centrifuge tube. Tubes were then centrifuged for 30 minutes at 600×g. Banded PBLs were gently aspirated from the resulting interface and subsequently washed 2× with PBS by low speed centrifugation. After final wash, cells were enumerated by trypan blue exclusion and re-suspended at 1×10$^7$/ml in RPMI 1640 with 15% Fetal Bovine Serum (FBS), 2 mM L-glutamine, 4 mg/ml PHA-P and allowed to incubate for 48–72 hours at 37° C. After incubation, PBLs were centrifuged and reset in RPMI 1640 with 15% FBS, 2 mM L-glutamine, 100 U/ml penicillin, 100 µg/ml streptomycin, 10 µg/ml gentamycin, and 20 U/ml recombinant human IL-2. PBLs were maintained in this medium at a concentration of 1–2×10$^6$/ml with bi-weekly medium changes, until use in assay protocol.

For the PBL assay, PHA-P stimulated cells from at least two normal donors were pooled, set in fresh medium at 2×10$^6$/ml, and plated in the interior wells of a 96 well round bottom microplate at 50 µL/well. Test drug dilutions were prepared at a 2× concentration in microtiter tubes, and 100 µl of each concentration was placed in appropriate wells in a standard format. Fifty microliters of a predetermined dilution of virus stock was placed in each test well. Wells with cells and virus alone were used for virus control. Separate plates were identically set without virus for drug cytotoxicity studies using an XTT assay system.

In the standard PBL assay (MOI: 0.2), the assay was ended on day 7 following collection of cell free supernatant samples for reverse transcriptase activity assay. In the low MOI PBL assay (MOI: 0.02), supernatant samples were collected on day 6, day 11, and day 14 post-infection and analyzed for RT activity. Tri013iated thymidine triphosphate (NEN) (TTP) was resuspended in distilled H$_2$O at 5 Ci/ml. Poly rA and oligo dT were prepared as a stock solution which was kept at −20° C. The RT reaction buffer was prepared fresh on a daily basis and consists of 125 µl 1 M DTT, and 40 µl 1 M MgCl$_2$. These three solutions were mixed together in a ratio of 2 parts TTP, 1 part poly rA:oligo dT, and 1 part reaction buffer. Ten microliters of this reaction mixture was placed in a round bottom microtiter plate and 15 µl of virus containing supernatant was added and mixed. The plate was incubated at 37° C. in a water bath with a solid support to prevent submersion of the plate and incubated for 60 minutes. Following reaction, the reaction volume was spotted onto pieces of DE81 paper, washed 5 times for 5 minutes each in a 5% sodium phosphate buffer, 2 times for 1 minute each in distilled water, 2 times for 1 minute each in 70% ethanol, and then dried. Opti-Fluor O was added to each sample and incorporated radioactivity was quantified utilizing a liquid scintillation counter, (Wallac 1450 Microbetaplus, Gaithersburg, Md.).

Tritiated thymidine incorporation was measured in parallel cultures at day 7. Each well was pulsed with 1 µCi of tritiated thymidine and the cells were harvested 18 hours later with a Skatron cell harvester onto glass fiber filter papers. The filters were dried, placed in a scintillation vial with 1 ml of scintillation cocktail and incorporated radioactivity was quantified on a liquid scintillation counter (e.g., Packard Tri-Carb 1900 TR450).

B. Assay in Fresh Human Monocyte-Macrophages

For isolation of adherent cells, 3×10$^6$ non-PHA stimulated peripheral blood cells were resuspended in Hanks buffered saline (with calcium and magnesium) supplemented with 10% human AB serum. The cells were placed in a 24-well microtiter plate at 37° C. for 2 hours. Non-adherent cells were removed by vigorously washing six times. The adherent cells were cultured for 7 days in RPMI 1640 tissue culture medium with 15% fetal bovine serum. The cultures were carefully monitored for confluency during this incubation period. Infection of the cells was performed with the monocytotropic HIV-1 strains BaL or ADA and the matched pair of AZT-sensitive and AZT-resistant virus isolates. Each of these virus isolates was obtained from the NIAID AIDS Research and Reference Reagent Program. High titer pools of each of these viruses have been harvested from infected cultures of peripheral blood adherent cells and frozen in 1.0 ml aliquots at −80° C. Monocyte-macrophage monolayers were infected at an MOI of 0.1. Compounds to be evaluated in the monocyte-macrophage assay are added to the monolayers shortly before infection in order to maximize the potential for identifying active compounds.

At 2 days post-infection, the medium was decanted and the cultures washed twice with complete medium in order to remove excess virus. Fresh medium alone or medium containing the appropriate concentrations of drugs was added and incubation continued for an additional 5 days. XTT-tetrazolium or trypan blue exclusion assays (for cell viability) and HIV p24 ELISA assays (for production of p24 core antigen) were performed on Day 7 post-infection. ELISA kits were purchased from Coulter. The assay is performed according to the manufacturer's recommendations. Control curves are generated in each assay to accurately quantify the amount of capsid protein in each sample. Data was obtained by spectrophotometric analysis at 450 nm using a plate reader (Molecular Devices Vmax). P24 concentrations were calculated from the optical density values by use of the Molecular Device software package Soft Max.

EXAMPLE 8

Inhibition of Acute Infection of MT-4 Cells

CPE based infection experiments were performed using MT-4 cells (Pauwels et al. (1988) *J. Virol. Meth.* 20:309; Papp et al. (1997) *AIDS Research and Human Retroviruses In Press*). MT-4 cells were obtained from the AIDS Research and Reference Reagent Bank, Division of AIDS, NIAID, NIH contributed Dr. Richman (Pauwels et al. (1988) *J. Virol. Meth.* 20:309) T-lymphoid H9 (HUT-78) cells were obtained from Dr. Robert Gallo, National Cancer Institute, Bethesda, Md. (Popovic et al. (1984) *Science* 224:497; Gazdar et al. (1980) *Blood* 55:409). Cell cultures were maintained in RPMI 1640 medium (GIBCO Laboratories, Grand Island, N.Y.) supplemented with 20% (H9 cells), or 10% (MT-4 cells) heat-inactivated fetal bovine serum (Sigma Chemical Co., St. Louis, Mo.) 250 units/ml penicillin, 250 µg/ml streptomycin, 2 mM 1-glutamine, and 10 mM HEPES (N-2-hydroxyethylpiperazine-N'-2-ethanesulfonic acid) buffer (complete medium) at 37° C. in 5% $CO_2$. HIV-1 IIB was originally obtained from Dr. Robert Gallo, National Cancer Institute (Popovic (1984) *Science* 224:497). Virus stocks of HIV-1 were prepared from cell-free filtered supernatant of chronically infected H9 cultures by the shaking method as previously described by Vujoie et al. (*J. Infectious Diseases* (1988) 157:1047).

Experiments were performed under two sets of conditions. Dilutions of hybrid oligonucleotides according to the invention having SEQ ID NO:1 were prepared in 96-well plates and infections were performed either in the presence of inhibitors, by adding MT-4 cells and a $TCID_{CPE-90\%}$ concentration of $HIV_{-HHB}$ directly to the wells, or by infecting MT-4 cells for 4 hours at 37° C. in the absence of inhibitors, washing to remove non-adsorbed virus, then adding the infected cells to wells containing inhibitors. The cultures were incubated for 6 days and CPE measured using the MTT dye method. (Rapid, (1983) *J. Immunolog. Meth.* 65:55).

The results demonstrate that an oligonucleotide of the invention inhibits HIV-1 infection when added to cells during viral infection (FIG. 1) or post-viral adsorption (FIG. 2).

EXAMPLE 9

Measurement of Orally Administered Oligonucleotide

A. Animals and Treatment

Male Sprague-Dawley rats (100–120 g, Harlan Laboratories, Indianapolis, Ind.) and male CD-/F2 mice (25±3 g, Charles River Laboratory, Wilmington, Mass.) are used in the study. The animals are fed with commercial diet and water ad libitum for 1 week prior to the study.

Unlabelled and $^{35}$S-labelled oligonucleotides are dissolved in physiological saline (0.9% NaCl) in a concentration of 25 mg/ml, and are administered to the fasted animals via gavage at the designated dose (30–50 mg/kg for rats and 10 mg/kg for mice). Doses are based on the pretreatment body weight and rounded to the nearest 0.01 ml. After dosing, each animal is placed in a metabolism cage and fed with commercial diet and water ad libitum. Total voided urine is collected and each metabolism cage is then washed following the collection intervals. Total excreted feces is collected from each animal at various timepoints, and feces samples are homogenized prior to quantitation of radioactivity. Blood samples are collected in heparinized tubes from animals at the various timepoints. Plasma is separated by centrifugation. Animals are euthanized by exsanguination under sodium pentobarbital anesthesia at various times (i.e., 1, 3, 6, 12, 24, and 48 hr; 3 animals/time point). Following euthanasia, the tissues are collected from each animal. All tissues/organs are trimmed of extraneous fat or connective tissue, emptied and cleaned of all contents, individually weighed, and the weights recorded.

To quantitate the total absorption of the hybrid oligonucleotide, two additional groups of animals (3/group) for each test oligonucleotide are treated using the same procedure as above. Animals are killed at 6 or 12 hr post dosing, and the gastrointestinal tract is then removed. Radioactivities in the gastrointestinal tract, feces, urine, plasma, and the remainder of the body is determined separately. Total recovery of radioactivity is also determined to be 95±6%. The percentage of the absorbed hybrid oligonucleotide-derived radioactivity is determined by the following calculation: (total radioactivity in the remainder of the body+total radioactivity in urine)÷(total radioactivity in the gastrointestinal tract, feces, urine, plasma, and the remainder of the body).

B. Radioactive Labelling of Oligonucleotide

To obtain $^{35}$S-labelled oligonucleotide, synthesis is carried out in two steps. The first nucleotides of the oligonucleotide sequence from its 3'-end are assembled using the β-cyanoethylphosphoramidite approach (see, Beaucage in *Protocols for Oligonucleotides and Analogs* (Agrawal, ed.), Humana Press, (1993), pp. 33–61). The last nucleotides are assembled using the H-phosphonate approach (see, Froehler in *Protocols for Oligonucleotides and Analogs* (Agrawal, ed.) Humana Press, 1993, pp. 63–80). Controlled pore glass (CPG) support-bound oligonucleotide (30 mg of CPG;

approximately 1 µM) containing five H-phosphonate linkage is oxidized with $^{35}S_8$ (4 mCi, 1 Ci/mg, Amersham; 1 Ci=37 GBq) in 60 ml carbon disulfide/pyridine/triethylamine (10:10:1). The oxidation reaction is performed at room temperature for 1 hr with occasional shaking. Then 2 µl, 5 µl, and 200 µl of 5% cold sulfur ($^{32}S_8$) in same solvent mixture is added every 30 min to complete the oxidation. The solution is removed and the CPG support is washed with carbon disulfide/pyridine/triethylamine (10:10:1) (3×500 µl) and with acetonitrile (3×700 µl). The product is deprotected in concentrated ammonium hydroxide (55° C., 14 hr) and evaporated. The resultant product is purified by polyacrylamide gel electrophoresis (20% polyacrylamide containing 7 M urea). The desired band is excised under UV shadowing and the PS-oligonucleotide was extracted from the gel and desalted with a Sep-Pak C18 cartridge (Waters) and Sephadex G-15 column.

C. Total Radioactivity Measurements

The total radioactivities in tissues and body fluids is determined by liquid scintillation spectrometry (LS 6000TA, Beckman, Irvine, Calif.). In brief, biological fluids (plasma, 50–100 µl; urine, 50–100 µl) are mixed with 6 ml scintillation solvent (Budget-Solve, RPI, Mt. Prospect, Ill.) to determine total radioactivity. Feces are ground and weighed prior to being homogenized in a 9-fold volume of 0.9% NaCl saline. An aliquot of the homogenate (100 µl) is mixed with solubilizer (TS-2, RPI, Mt. Prospect, Ill.) and then with scintillation solvent (6 ml) to permit quantitation of total radioactivity.

Following their removal, tissues are immediately blotted on Whatman No. 1 filter paper and weighed prior to being homogenized in 0.9% NaCl saline (3–5 ml per gram of wet weight). The resulting homogenate (100 µl) is mixed with solubilizer (TS-2, RPI, Mt. Prospect, Ill.) and then with scintillation solvent (6 ml) to determine total radioactivity. The volume of 0.9% NaCl saline added to each tissue sample is recorded. The homogenized tissues/organs are kept frozen at ≦−70° C. until the use for further analysis.

D. HPLC Analysis

The radioactivity in urine is analyzed by paired-ion HPLC using a modification of the method described essentially by Sands et al. (Mol. Pharm. (1994) 45:932–943). Urine samples are centrifuged and passed through a 0.2-µm Acro filter (Gelman, Ann Arbor, Mich.) prior to analysis. Hybrid oligonucleotide and metabolites in plasma samples are extracted using the above methods in sample preparation for PAGE. A Microsorb MV-C4 column (Rainin Instruments, Woburn, Mass.) is employed in HPLC using a Hewlett Packard 1050 HPLC with a quaternary pump for gradient making. Mobile phase includes two buffers; Buffer A was 5 mM-A reagent (Waters Co., Bedford, Mass.) in water and Buffer B is 4:1 (v/v) Acetonitrile (Fisher)/water. The column is eluted at a flow rate of 1.5 ml/min, using the following gradient: (1) 0–4 min, 0% buffer B; (2) 4–15 min 0–35% Buffer B; and (3) 15–70 min 35%-80% Buffer B. The column is equilibrated with Buffer A for at least 30 min prior to the next run. By using a RediFrac fraction collector (Pharmacia LKB Biotechnology, Piscataway, N.J.), 1-min fractions (1.5 ml) are collected into 7-ml scintillation vials and mixed with 5 ml scintillation solvent to determine radioactivity in each fraction.

E. Analysis of Test Oligonucleotides

Polyacrylamide gel electrophoresis (PAGE) of oligonucleotides and its metabolites is carried out by known and established methods. Plasma and tissue homogenates are incubated with proteinase K (2 mg/ml) in extraction buffer (0.5% SDS/10 mM NaCl/20 mM Tris-HCl, pH 7.6/10 mM EDTA) for 1 hr at 60° C. The samples are then extracted twice with phenol/chloroform (1:1, v/v) and once with chloroform. After ethanol precipitation, the extracts are analyzed by electrophoresis in 20% polyacrylamide gels containing 7 M urea. Urine samples are filtered, desalted and then analyzed by PAGE. The gels are fixed in 10% acetic acid/10% methanol solution and then dried before autoradiography.

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

What is claimed is:

1. A method of treating HIV-1 or HIV-2 infection in a mammal, comprising the step of administering to the mammal a synthetic oligonucleotide in an amount effective to inhibit the proliferation of HIV-1 or HIV-2, the oligonucleotide being specifically complementary to nucleotides 324 to 345 of a conserved gag region of the HIV-1 genome set forth as SEQ ID NO: 5, and consisting of 21 nucleotides which are linked ia phosphorothioate internucleotide linkages.

2. A method of treating HIV-1 or HIV-2 infection in a human comprising administering intravenously to the human a synthetic oligonucleotide in an amount effective to inhibit the proliferation of HIV-1 or HIV-2, the oligonuceotide comprising a nucleotide sequence consisting of 21 nucleotides of the sequence set forth as SEQ ID NO: 5, the nucleotides being linked via phosphorothioate internucleotide linkages, and the oligonucleotide being specifically complementary to nucleotides 9 to 30 of SEQ ID NO. 8, which comprises a conserved gag region of the HIV-1 genome.

3. A method of treating HIV-1 or HIV-2 infection in a human comprising administering intravenously to the human a synthetic oligonucleotide in an amount effective to inhibit the proliferation of HIV-1 or HIV-2, the oligonuceotide comprising a nucleotide sequence consisting of 21 nucleotides of the sequence set forth as SEQ ID NO: 5, the nucleotides being linked via phosphorothioate internucleotide linkages, and the oligonucleotide being specifically complementary to nucleotides 9 to 30 of SEQ ID NO. 8, which comprises a conserved gag region of the HIV-1 genome.

* * * * *

SEQUENCE LISTING

```
<160> NUMBER OF SEQ ID NOS: 8
<210> SEQ ID NO 1
<211> LENGTH: 21
<212> TYPE: DNA/RNA
<213> ORGANISM: Artificial Sequence
<220> FEATURE:
<223> OTHER INFORMATION: synthetic modified antisense oligonucleotide

<400> SEQUENCE: 1
ucgcacccat ctctctccuu c                                              21

<210> SEQ ID NO 2
<211> LENGTH: 21
<212> TYPE: DNA
<213> ORGANISM: Artificial Sequence
<220> FEATURE:
<223> OTHER INFORMATION: synthetic modified antisense oligonucleotide

<400> SEQUENCE: 2
```

```
tcgcacccat ctctctcctt c                                              21

<210> SEQ ID NO 3
<211> LENGTH: 21
<212> TYPE: DNA/RNA
<213> ORGANISM: Artificial Sequence
<220> FEATURE:
<223> OTHER INFORMATION: synthetic modified antisense oligonucleotide

<400> SEQUENCE: 3
cgcacccatc tctctccuuc u                                              21

<210> SEQ ID NO 4
<211> LENGTH: 21
<212> TYPE: DNA
<213> ORGANISM: Artificial Sequence
<220> FEATURE:
<223> OTHER INFORMATION: synthetic modified antisense oligonucleotide

<400> SEQUENCE: 4
cgcacccatc tctctccttc t                                              21

<210> SEQ ID NO 5
<211> LENGTH: 22
<212> TYPE: DNA
<213> ORGANISM: Artificial Sequence
<220> FEATURE:
<223> OTHER INFORMATION: synthetic modified antisense oligonucleotide

<400> SEQUENCE: 5
tcgcacccat ctctctcctt ct                                             22

<210> SEQ ID NO 6
<211> LENGTH: 21
<212> TYPE: DNA/RNA
<213> ORGANISM: Artificial Sequence
<220> FEATURE:
<223> OTHER INFORMATION: synthetic modified oligonucleotide

<400> SEQUENCE: 6
tcgcacccat ctctctcctt c                                              21

<210> SEQ ID NO 7
<211> LENGTH: 22
<212> TYPE: DNA
<213> ORGANISM: HIV-1

<400> SEQUENCE: 7
tcttcctctc tctacccacg ct                                             22

<210> SEQ ID NO 8
<211> LENGTH: 41
<212> TYPE: DNA
<213> ORGANISM: HIV-1

<400> SEQUENCE: 8
cggaggctag aaggagagag atgggtgcga gagcgtcagt a                        41
```